United States Patent
Ouadi et al.

(10) Patent No.: US 7,045,606 B2
(45) Date of Patent: May 16, 2006

(54) BIFUNCTIONAL CHELATING AGENT FOR ACTINIUM

(75) Inventors: Ali Ouadi, Strasbourg (FR); Jean-Francois Gestin, Mauves sur Loire (FR); Christos Apostolidis, Heidelberg (DE)

(73) Assignee: European Community, Brussels (BE)

( * ) Notice: Subject to any disclaimer, the term of this patent is extended or adjusted under 35 U.S.C. 154(b) by 0 days.

(21) Appl. No.: 10/488,938

(22) PCT Filed: Sep. 13, 2002

(86) PCT No.: PCT/EP02/10306

§ 371 (c)(1),
(2), (4) Date: Mar. 16, 2004

(87) PCT Pub. No.: WO03/024940

PCT Pub. Date: Mar. 27, 2003

(65) Prior Publication Data

US 2004/0242852 A1    Dec. 2, 2004

(30) Foreign Application Priority Data

Sep. 17, 2001    (LU) ........................................ 90834

(51) Int. Cl.
*C07K 16/00* (2006.01)
*C07D 259/00* (2006.01)
*G01N 33/534* (2006.01)
*C12N 9/96* (2006.01)
*A61K 51/00* (2006.01)

(52) U.S. Cl. .................. 530/391.5; 530/405; 530/409; 540/474; 436/545; 424/9.36; 424/9.364; 588/20; 588/318; 435/188

(58) Field of Classification Search .............. 540/474; 530/391.5, 404, 405, 409; 436/545; 424/9.36, 424/9.364; 588/20, 318; 435/188
See application file for complete search history.

(56) References Cited

FOREIGN PATENT DOCUMENTS

| WO | 95 20580 | 8/1995 |
|----|----------|--------|
| WO | 00 59896 | 10/2000 |
| WO | 01 68618 | 9/2001 |

OTHER PUBLICATIONS

Schumann, Herbert et al: "1,4,7,10,13,16,19,22-octaazacyclotetracosane-1,4,7,10,13,16,19,22-octaacetic acid (H8OTEC) and 1,4,7,10,14,17,20,23-octaazacyclohexacosane-1,4,7,10,14,17,20,23-octaacetic acid (H8OHEC). Synthesis and characterization of two large macrocyclic polyamine polycarboxylic ligands" Chem. Ber./ Recl. (1997), 130 (2), 267-277, 1997, XP002199523 the whole document.

Ouadi A et al: "Synthesis of a novel bifunctional chelating agent for actinium complexation" Tetrahedron Letters, Elsevier Science Publishers, Amsterdam, NL, vol. 41, No. 37, Sep. 2000, pp. 7207-7209, XP004210234 ISSN: 0040-4039 cited in the application the whole document.

*Primary Examiner*—Long V. Le
*Assistant Examiner*—Shafiqul Haq
(74) *Attorney, Agent, or Firm*—Oblon, Spivak, McClelland, Maier & Neustadt, P.C.

(57) ABSTRACT

The invention concerns a ligand comprising (I) wherein n is an integer from 1 to 5 Y is CO2H or PO3H2 T represents —X or -phenyl-X, wherein X represents NO2, NH2, NCS, NHCOCH2-Z, NHCO—W—COCNHS, —NH-Q, —NHCS-Q, —NHCOCH2-Q, or NHCO(CH2)m-Q where Q is a hapten chosen from the group consisting of steroids, enzymes, proteins, monoclonal antibodies, chimeric antibodies, or fragments thereof or any activated linker ready for coupling reaction, W is —(CH2)m- m is an integer from 1 to 10 Z is chloride, bromide or iodine

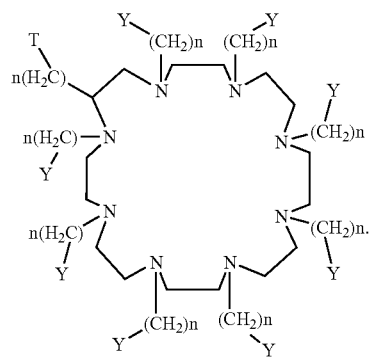

4 Claims, 1 Drawing Sheet

BIFUNCTIONAL CHELATING AGENT FOR ACTINIUM

TECHNICAL FIELD

The present invention relates to bifunctional chelating agents and more particular to bifunctional polyaza polycarboxylic or polyphosphonic macrocycles ligands a method of synthesis of these products and their uses.

BACKGROUND OF THE INVENTION

As described by Davis, I. A. et al in the article "Comparison of Actinium 225 Chelates: Tissue Distribution and Radiotoxicity" published in Nucl. Med. Biol., Vol. 26, pp 581–589, 1999; by Deal, K. A. et al. in the article "Improved in Vivo stability of Actinium-225 Macrocyclic Complexes" published in J. Med. Chem., Vol. 42, pp. 2988–2992, 1999, by Grote Gansey, M. H. B. et al. in the article "Conjugation, Immunoreactivity, and Immunogenicity of Calix (4) arenes; Model Study to Potential Calix (4) arenes—Based Ac3+ Chelators" published in Bioconj. Chem., Vol. 10, pp 610–623, 1999, and by Ouadi, A. et al. in the article "Synthesis of a novel Bifunctional Chelating Agent for 225Ac complexation" published in Tet. Lett., Vol 41 pp 7202–7209, 2000, a bifunctional chelating agent is necessary to bind with a good stability a radionuclide to a vector.

An object of the invention is to provide more effective bifunctional chelating agents for metals especially actinides and lanthanides.

SUMMARY OF THE INVENTION

The present invention includes a ligand comprising:

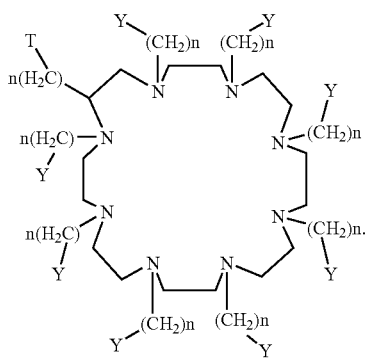

wherein
n is an integer from 1 to 5
Y is —$CO_2H$ or —$PO_3H_2$
T represents —X or -phenyl-X, wherein
X represents —$NO_2$, —$NH_2$, —NCS, —$NHCOCH_2$—Z, —NHCO—W—COCNHS, —NH—Q, —NHCS—Q, —$NHCOCH_2$—Q, or —$NHCO(CH_2)_m$—Q where Q is a hapten chosen from the group consisting of steroids, enzymes, proteins, monoclonal antibodies, chimeric antibodies, or fragments thereof or any activated linker ready for coupling reaction,
W is —$(CH_2)_m$—
m is an integer from 1 to 10
Z is chloride, bromide or iodine.
If X represents —NH—Q, —NHCS—Q, —NHCOCH₂—Q, or —$NHCO(CH_2)_m$—Q where Q is a hapten chosen from the group consisting of steroids, enzymes, proteins, monoclonal antibodies, chimeric antibodies, humanised antibodies or fragments thereof, the resulting ligand is also called a ligand-hapten conjugate.

The invention also includes according to a preferred embodiment, a metal chelate of the ligand as described above wherein the metal is actinium-225 ($^{225}$Ac).

The present invention also includes the method of using the metal chelates of the ligand-hapten conjugate possessing a linking group wherein the chelate as a therapeutic or diagnostic agent.

Specifically, such ligands are useful for radiolabeling proteins with radioactive metals, and can consequently be utilised with respect to radioimmunoimaging and/or radioimmunotherapy. The present ligand-hapten conjugates firmly link actinium to proteins, minimise metal release and permit high selective delivery of metals to targeted sites in vivo. This is especially true for the actinium complexation metal chelate protein conjugates.

Immunotherapy with radiolabelled antibodies allows fairly specific targeting of certain cancers (see e.g. Couturier, O. et al. "Validation of 213-Bi-alpha radioimmunotherapy for multiple myeloma" in Clin. Cancer. Res., Vol. 5, pp. 3165–3170, 1999; Huneke, R. B., et al. in "Effective alpha-particle-mediated radioimmunotherapy of murine leukemia" in Cancer Res., Vol. 52, pp. 5818–5820, 1992; Kennel, S. J. et al. "Radioimmunotherapy of micrometastases in lung with vascular targeted 213Bi" in Br. J. Cancer, Vol. 80, pp. 175–184, 1999; Kozak, R. W. et al. "Bismuth-212-labeled anti-Tac monoclonal antibody: alpha-particle-emitting radionuclides as modalities for radioimmunotherapy" in Proc. Natl. Acad. Sci. USA, Vol. 83, pp. 474–478, 1986 or Macklis, R. M. et al. "Radioimmunotherapy with alpha-particle-emitting immunoconjugates" in Science, Vol. 240, pp. 1024–1026, 1988).

This technique is based on the use of radionuclides associated to antibodies or peptides that are specific of antigens expressed on the tumor cells. In order to bind a radionuclide to a vector it is necessary to use bifunctional chelating agents (BCA) that have two specific sites. One site is to be coupled to the vector and the other has to form very stable complexes with the radionuclide to be used.

$^{225}$Ac, which is an alpha emitter, is a good candidate for such applications as described by Kaspersen, F. M. et al. "Cytotoxicity of 213Bi- and 225Ac-immunoconjugates" in Nucl. Med. Commun., Vol. 16, pp. 468–476, 1995. The very short range (<100 μm) of α-particles and the high energy transfer allows efficient destruction of tumor cells whereas normal cells are relatively spared.

Chelators that can hold radioactive metals with high stability under physiological conditions are essential to avoid excessive radiation damage to non-target cells.

Furthermore, these bifunctional chelating agents allow different applications; it can be used to bind $^{225}$Ac to any biological or non-biological structures for any applications.

These chelating agents can be used non-associated to a vector as a detoxication chelating agent or using the natural tropism of the complex.

This chelating agent can also be used grafted on a chromatographic column in order to purify or concentrate any solutions containing $^{225}$Ac.

The complexation properties of our product with $^{225}$Ac show that this chelating agent may also be useful as a good extractant in the process of separation of minor actinides and lanthanides in nuclear waste or to separate specific groups of metals in high level waste.

BRIEF DESCRIPTION OF THE DRAWINGS

Embodiments of the present invention are described by way of example and with reference to the accompanying drawing wherein.

An access route that allows the synthesis of a bifunctional macrocycle chelating agent is described in FIG. 1.

DETAILED DESCRIPTION

Figure 1:
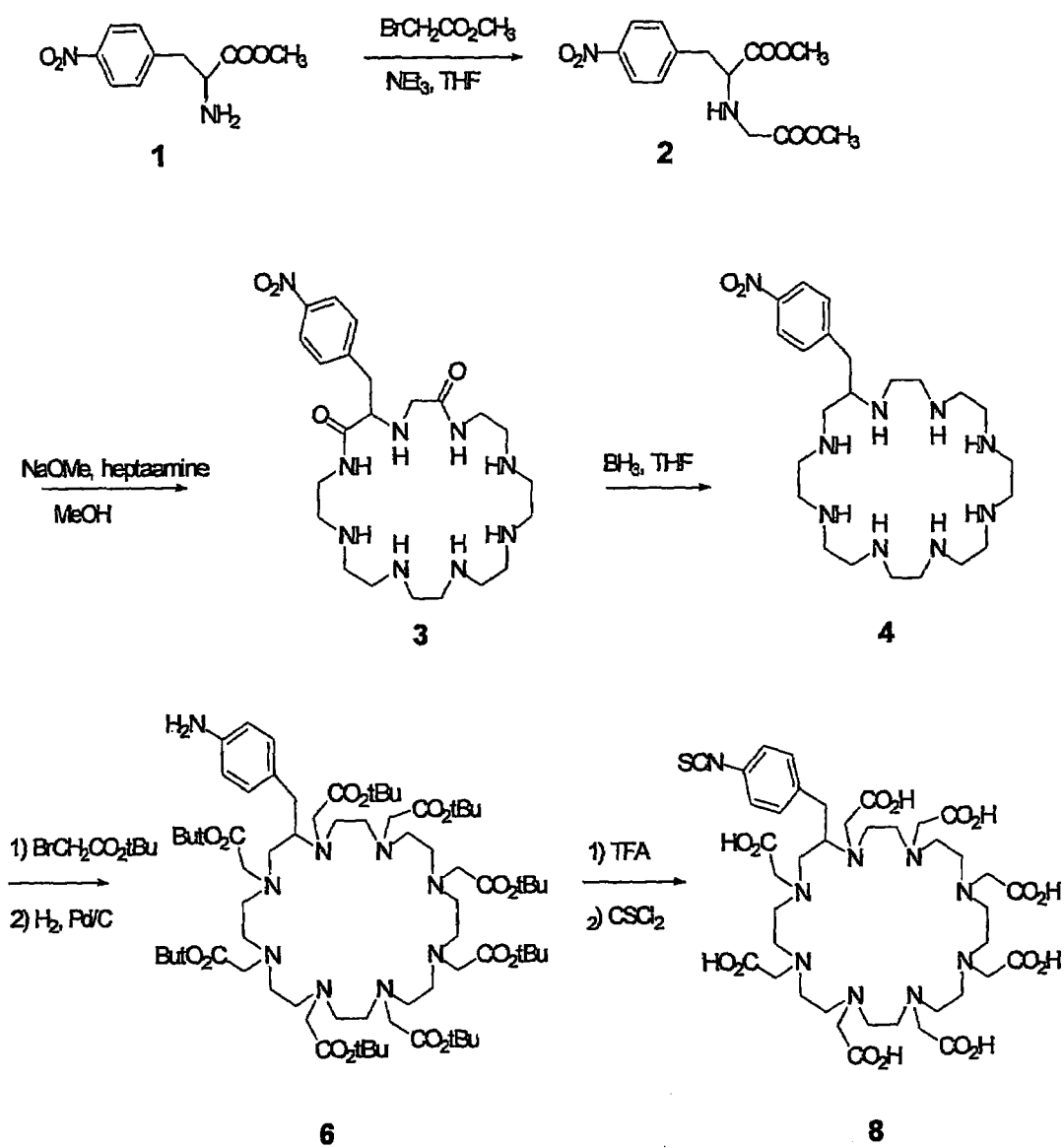
FIG. 1 represents a scheme for the preparation of a substituted 1,4,7,10,13,16,19,22-octa(2-carboxymethyl)-octaaazacyclotétracosane ligand (8).

Different non-functionalised chelating agents (commercially available or readily synthesised in the laboratory) bearing aminocarboxylate groups (EDTA, DTPA, DOTA, PEPA, HEHA and HOHEC) or aminophosphonate groups (EDTMP) were tested for their complexation properties with $^{225}$Ac. It was found that HOTEC compound (1,4,7,10,13, 16,19,22-octacarboxylmethyl-1,4,7,10,13,16,19,22-octaaazacyclotetracosane) appeared to be the best candidate for $^{225}$Ac complexation. This result is in balance in regard of previous studies. Polyaza polycarboxylic macrocycles are known to form thermodynamically stable complexes with large metal ions such as actinides and lanthanides.

EXAMPLE

N-((Methoxycarbonyl)methyl)-4-nitrophenylalanine methyl ester (2)

Triethylamine (22 mmol) was added to a suspension of 4-nitrophenylalanine methyl ester hydrochloride (1) (21 mmol) in THF (50 ml). The mixture was stirred at room temperature for one hour, the triethylamine hydrochloride was filtered off, and the filtrate concentrated to yellow oil. The oil was dissolved in dry THF (50 ml) and to this solution was added triethylamine (60 mmol) and methylbromoacetate (60 mmol), the solution was stirred at room temperature under nitrogen atmosphere for 3 hours, after which the precipitate was filtered off and the filtrate concentrated on vacuum. The residue was dissolved in ethylacetate, washed with $H_2O$, dried (MgSO$_4$) and concentrated on vacuum to give yellow oil.

Compound (3)

Sodium (20 mmol) was dissolved in dry methanol (100 ml) at room temperature under nitrogen atmosphere and to this solution was added hexaethyleneheptamine (18 mmol) and N-((methoxycarbonyl)methyl)-4-nitrophenylalanine methyl ester (2) (18 mmol). This solution was refluxed for 72 hours after which the solvent was removed and the residue was purified on silica gel chromatography with chloroforme/methanol/NH$_3$ (aq) (75:20:5).

Compound (4)

A solution of BH$_3$ in THF (100 mmol) was added dropwise to a stirred suspension of (3) (10 mmol) in THF (50 ml) at 0° C. under nitrogen atmosphere. The solution was heated at reflux for 36 hours. Methanol was added slowly to the solution at 0° C. after which the solvent was removed and the residue was dissolved in methanol (50 ml); the resulting mixture was cooled at 0° C. and gaseous HCl was bubbled through the solution and then the mixture was refluxed for 12 hours. The resulting precipitate was collected washed with ether to give a white powder. The solid was dissolved in water and was loaded on a column of DOWEX 1X-8 anion-exchange resin (OH$^-$ form). The column was eluted with water; alkaline fractions were collected, and the water was removed under vacuum Compound (5)

To a solution of (4) (10 mmol) in DMF (50 ml) at room temperature under a nitrogen atmosphere was added anhydrous sodium carbonate (0.11 mol) and a solution of tert-butyl bromoacetate (62 mmol) in DMF (20 ml). The mixture was heated at 60° C. for 18 hours after which the solvent was removed and the residue was dissolved in chloroform washed with brine, dried (MgSO$_4$) and concentrated on vacuum.

Compound (6)

To a solution of (5) (15 mmol) in ethanol (50 ml) at room temperature was added Pd/C under H$_2$ atmosphere. The mixture was refluxed for 2 hours, the residue was passed over Celite. The filtrate was evaporated on vacuum.

Compound (8)

(10 mmol) of (6) was treated with TFA (0.1 mol) 6 hours at room temperature under nitrogen atmosphere after which the solvent was removed.

The compound thus obtained was dissolved in water and loaded on a column of DOWEX 50WX8-200 (H$^+$form).

The column was eluted consecutively with 0.5 M HCl and with water until the eluent was neutral and finally with 0.5 M aqueous ammonia solution. Alkaline fractions were collected, and the water was removed on vacuum The compound thus obtained was dissolved in water and the pH was adjusted to 9.0 with NaHCO$_3$. To this solution was added at room temperature under nitrogen atmosphere thiophosgene in CHCl$_3$ (10 ml), the mixture was stirred for 2 hours. The organic layer was removed and the water was evaporated on vacuum to give the final product (8).

While a preferred embodiment of the present invention has been described, it will apparent to those skilled in the art that many changes and modifications may be made without departing from the invention in its broader aspects. The appended claims are therefore intended to cover all such changes and modifications as fall within the true spirit and scope of the invention.

What is claimed is:

1. A ligand comprising:

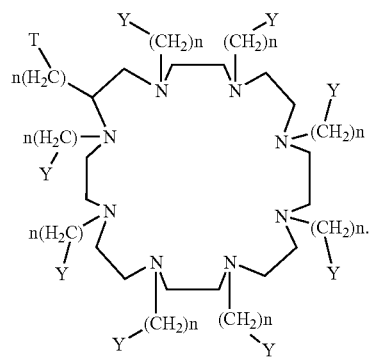

wherein
n is an integer ranging from 1 to 5
Y is —CO$_2$H or —PO$_3$H$_2$
T represents —X or —phenyl—X, wherein
X represents —NO$_2$, —NH$_2$, —NCS, —NHCOCH$_2$—Z, —NHCO—W—COCNHS, —NH-Q, —NHCS—Q, —NHCOCH$_2$—Q, or —NHCO(CH$_2$)$_m$—Q, where Q is a hapten selected from the group consisting of steroids, enzymes, proteins, monoclonal antibodies, chimeric antibodies, fragments thereof and any activated linker ready for coupling reaction,
W is —(CH$_2$)$_m$—
m is an integer ranging from 1 to 10, and
Z is chloride, bromide or iodine.

2. A metal chelate, comprising:
actinium chelated by the ligand of claim 1.

3. The metal chelate of claim 2, wherein the actinium is actinium-225 ($^{225}$Ac).

4. A ligand comprising:

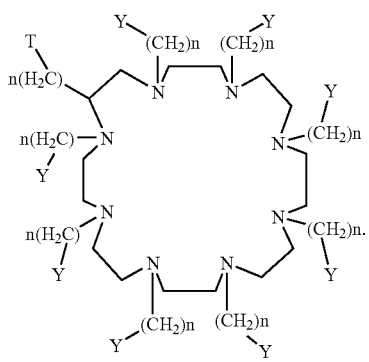

wherein
n is an integer ranging from 1 to 5
Y is —$CO_2H$ or —$PO_3H_2$
T represents —X or —phenyl—X, wherein
X represents —NH—Q, —NHCS—Q, —NHCOCH$_2$—Q, or —NHCO(CH$_2$)$_m$—Q, where Q is a hapten selected from the group consisting of steroids, enzymes, proteins, monoclonal antibodies, chimeric antibodies, fragments thereof and any activated linker ready for coupling reaction,
W is —(CH$_2$)$_m$—, and
m is an integer ranging from 1 to 10.

* * * * *